United States Patent
Tatsumi et al.

(10) Patent No.: US 7,405,315 B2
(45) Date of Patent: Jul. 29, 2008

(54) MESOPOROUS SILICA AND PROCESS FOR PRODUCING THE SAME

(75) Inventors: Takashi Tatsumi, Yokohama (JP); Hideaki Yoshitake, Tokyo (JP); Toshiyuki Yokoi, Yokohama (JP); Shunai Che, Yokohama (JP); Kazutami Sakamoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 498 days.

(21) Appl. No.: 10/716,427

(22) Filed: Nov. 20, 2003

(65) Prior Publication Data
US 2004/0267038 A1 Dec. 30, 2004

(30) Foreign Application Priority Data
May 21, 2003 (JP) .............................. 2003-144187

(51) Int. Cl.
*C07F 7/04* (2006.01)
(52) U.S. Cl. .................................................... 556/413
(58) Field of Classification Search ............ 501/53; 427/452, 503
See application file for complete search history.

(56) References Cited

U.S. PATENT DOCUMENTS
5,858,457 A * 1/1999 Brinker et al. .............. 427/162

OTHER PUBLICATIONS

Template-directed synthesis of bi-functionalized organo-MCM-41 and phenyl-MCM-48 silica mesophases Simon R. Hall, Christabel E. Fowler Benedicte Lebeau and Stephen Mann Chem. Commun., 1999,201-202.*

* cited by examiner

*Primary Examiner*—Samuel A Barts
(74) *Attorney, Agent, or Firm*—Oblon, Spivak, McClelland, Maier & Neustadt, P.C.

(57) ABSTRACT

(A) An anionic surfactant, (B) a silicate monomer and (C) a basic silane are mixed in water or a mixed solvent of a water-miscible organic solvent and water to obtain a mesoporous silica complex having mesopores with a uniform size, the anionic surfactant Component (A) is removed by washing the resultant mesoporous silica complex with an acidic aqueous solution, a water-miscible organic solvent or an aqueous solution thereof to obtain a mesoporous silica outer shell utilizing the structure of the mesoporous silica complex as a template, and the mesoporous silica complex or the mesoporous silica outer shell is calcined to obtain a mesoporous silica. The mesoporous silica can be synthesized in this manner utilizing the anionic surfactant micelle with a remarkably low affinity to the silicate monomer.

9 Claims, 13 Drawing Sheets

| | Neutralization | Double decomposition |
|---|---|---|
| Surfactant | ∼∼∼∼∼∼A⁻H⁺ | ∼∼∼∼∼∼A⁻ M⁺ |
| CSDA | $H_2N\text{—}\text{—}Si(OCH_3)_3$ (APS) | $(CH_3)_3N^+\text{—}\text{—}Si(OCH_3)_3\ Cl^-$ (TMAPS) |
| Interaction | [diagram of APS interaction] | [diagram of TMAPS interaction] |
| | ∼∼∼∼∼ : $C_nH_{2n+1}$, $C_nH_{2n+1}\text{-C(=O)-NH-CH(R_1)-}$,  $C_nH_{2n+1}\text{-C(=O)-NH-CH-}$ with side chain $\text{-AH}$ | |
| | A: $COO$, $OSO_3$, $SO_3$, $OPO_3$; $M^+$: $Na^+$, $K^+$, $NH_3^+\text{—}$ etc.; $R_1$: $H$, $CH_3$; $n = 8 - 18$; | |

FIG. 10

Supporting on line materials:

MESOPOROUS SILICA AND PROCESS FOR PRODUCING THE SAME

BACKGROUND OF THE INVENTION

1. Technical Field of the Invention

The present invention relates to a mesoporous silica utilizing the structure of a self-assembled anionic surfactant as the template, characterized by using a basic silane, and a process for producing the same.

2. Related Art

Mesoporous silicas such as MCM-41, wherein surfactant micelle has been utilized as the template, have high specific surface area and uniform pore size, and they have been applied in various fields because of their structural features. Methods for synthesizing the mesoporous silicas utilizing cationic or nonionic surfactants as templates have been well established (JP-A-2001-261326).

Anionic surfactants are higher in versatility and advantageous in costs and diversity as compared with the other three types of surfactants, i.e., cationic, nonionic and amphoteric surfactants. Although it has been reported that anionic surfactants can be used as a template in the same manner as for the other three types of surfactants to produce mesoporous metal oxides of iron, nickel, cobalt, etc. with three-dimensionally unstable, lamellar, mesoporous structures (Takashi Tatsumi, et al, *Materials Integration*, P. 50, Vol. 13, No. 10 (2000), and Q. Huo, G. D. Stucky, et al, *Chem. Mater.*, 1994, 6, 1176-1191), mesoporous silicas using the anionic surfactant templates have not been reported. Thus, the mesoporous silicas could not be synthesized using anionic surfactants practically. The reason therefor seems because silicate monomers have little affinity for the anionic surfactants, whereby the silicate monomers are polymerized not on the boundary surface of the micelle or self-assembly of the anionic surfactants but in solvent bulk under alkaline conditions. The thus-produced silicate has an amorphous structure similar to the polymerizate under alkaline conditions without surfactants.

SUMMARY OF THE INVENTION

Problems to be Solved by the Invention

The objective of the present invention is to synthesize a mesoporous silica using an anionic surfactant micelle as the template, the anionic surfactant having a remarkably low affinity for a silicate monomer.

Means to Solve the Problems

As a result of their intense research in view of the objective described in the preceding section, the inventors have found that a basic silane can increase the affinity of a silicate monomer for an anionic surfactant micelle, thereby accomplishing the objective. The present invention has been completed by these findings.

Thus, the invention comprises the following embodiments.

1) A basic silane for use in production of a mesoporous silica utilizing an anionic surfactant micelle, characterized in that it is represented by the following general formula (1).

   (1)

where $R^1$, $R^2$, $R^3$ and $R^4$ represent a straight-chain or branched-chain alkyl group or a hydrogen atom, and X represents a straight-chain or branched-chain alkylene group. When $R^4$ has the carbon atom number of 0, the basic silane, i.e., Component (C), corresponds to a primary, secondary or tertiary amine.

2) A mesoporous silica complex characterized by being derived from the following Components (A), (B) and (C):
(A) An anionic surfactant,
(B) A silicate monomer, and
(C) A basic silane.

3) The mesoporous silica complex according to 2) above, characterized in that said Component (C) is the basic silane as set forth in 1) above.

4) A mesoporous silica outer shell characterized by being derived from the following Components (A), (B) and (C):
(A) An anionic surfactant,
(B) A silicate monomer, and
(C) A basic silane.

5) The mesoporous silica outer shell according to 4) above, characterized in that said Component (C) is the basic silane as set forth in 1) above.

6) A mesoporous silica characterized by being derived from the following Components (A), (B) and (C):
(A) An anionic surfactant,
(B) A silicate monomer, and
(C) A basic silane.

7) The mesoporous silica according to 6) above, characterized in that said Component (C) is the basic silane as set forth in 1) above.

8) A method for producing a mesoporous silica complex, characterized in that said Components (A), (B) and (C) are mixed in water or a mixed solvent of a water-miscible organic solvent and water.

9) A method for producing a mesoporous silica outer shell, characterized in that said mesoporous silica complex obtained by the method according to 8) above is washed with an acidic aqueous solution, a water-miscible organic solvent, or an aqueous solution thereof, to remove the anionic surfactant, i.e., said Component (A).

10) A method for producing a mesoporous silica, characterized in that said mesoporous silica complex obtained by the method according to 8) above is calcined.

11) A method for producing a mesoporous silica, characterized in that said mesoporous silica outer shell obtained by the method according to 9) above is calcined.

BRIEF DESCRIPTION OF THE DRAWINGS

FIG. 10 is a schematic illustration of the two types of amino group-anionic surfactant head group interactions: through neutralization of acid with primary aminosilane APS and double decomposition of negatively charged anionic salt surfactant with positively charged quaternized aminosilane TMAPS.

DETAILED DESCRIPTION OF THE INVENTION

Figure 1:
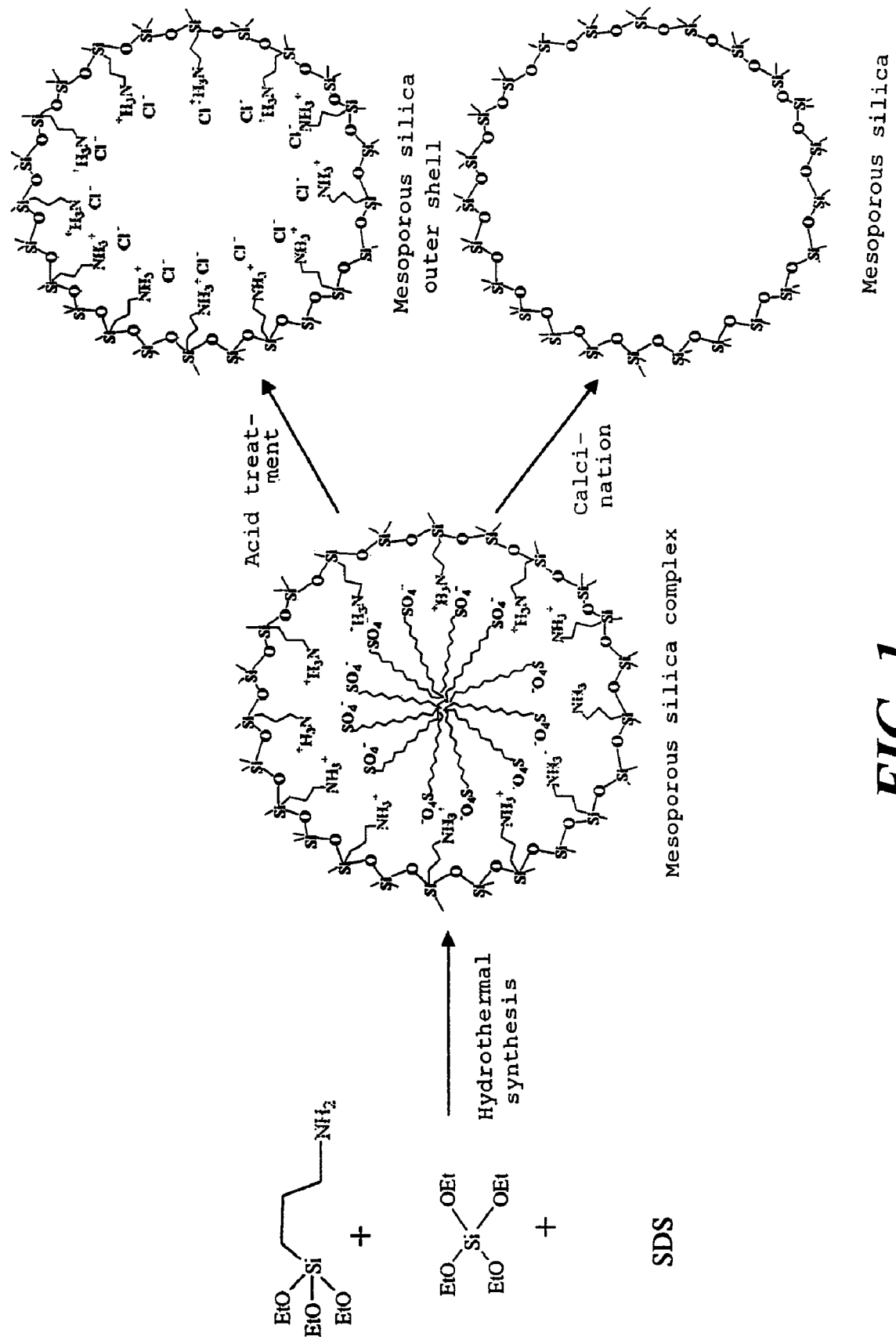
FIG. 1 illustrates the 3 Components according to the present invention and the relationships among a mesoporous silica complex, a mesoporous silica outer shell and a mesoporous silica.

The present invention will be described in detail below.

The Component (A) anionic surfactants to be used according to the invention are not particularly restricted, and various anionic surfactants to be exemplified and described below are usable according to the invention.

Examples of carboxylic acid salt-type anionic surfactants include alkyl carboxylic acid salt-type surfactants, N-acylaminocarboxylic acid salt-type surfactants, ether carboxylic acid salt-type surfactants, etc.

In the alkyl carboxylic acid salt-type anionic surfactants, the alkyl group is an alkyl residue of a saturated or unsaturated fatty acid having 6 to 22 carbon atoms. Examples of such fatty acids include lauric acid, myristic acid, palmitic acid, stearic acid, oleic acid, and the like, with a single composition. Further, the alkyl group may be an alkyl residue of natural mixed fatty acids such as coconut oil fatty acids, tallow fatty acids, hydrogenated tallow fatty acids, castor oil fatty acids, olive oil fatty acids, palm oil fatty acids, or the like, or synthetic fatty acids (including branched-chain fatty acids). The alkyl group may be a fluoroalkyl group in which the hydrogen atom(s) is or are randomly replaced by fluorine atom(s), in the present invention.

In the N-acylaminocarboxylic acid salt-type anionic surfactants, the acyl group is an acyl residue of a saturated or unsaturated fatty acid having 8 to 22 carbon atoms. Examples of such fatty acids include lauric acid, myristic acid, palmitic acid, stearic acid, oleic acid, and the like, with a single composition. Further, the acyl group may be an acyl residue of natural mixed fatty acids such as coconut oil fatty acids, tallow fatty acids, hydrogenated tallow fatty acids, castor oil fatty acids, olive oil fatty acids, palm oil fatty acids, or the like, or synthetic fatty acids (including branched-chain fatty acids). Examples of the aminocarboxylic acids to which the acyl group bonds include acidic amino acids such as glutamic acid, aspartic acid, cysteic acid, homocysteic acid and the like; neutral amino acids such as glycine, alanine, valine, leucine, isoleucine, phenylalanine, tryptophane, sarcosine, β-alanine, γ-aminobutyric acid, ε-aminocaproic acid, serine, homoserine, tyrosine, proline, hydroxyproline, cystine, cysteine, methionine and the like; and basic amino acids such as lysine, ornithine, arginine and the like; and the like. These acylated carboxylic acids may be used as an optically active isomer or a racemic body.

Examples of the ether carboxylic acid salt-type anionic surfactants include polyoxyethylene alkyl ether acetic acid salts, polyglyceryl alkyl ether acetic acid salts, and the like. Specific examples thereof include polyoxyethylene lauryl ether acetic acid salt, polyoxyethylene tridecyl ether acetic acid salt, etc.

Examples of sulfonic acid salt-type anionic surfactants include sulfosuccinic acid salt-type anionic surfactants, monobasic acid-type organic sulfonic acid salt-type anionic surfactants such as alkyl sulfonic acid salt-type, ester sulfonic acid salt-type, N-acylamino sulfonic acid salt-type surfactants and the like.

Examples of the above-mentioned sulfosuccinic acid salt-type anionic surfactants include sulfosuccinate esters of higher alcohols or ethoxylates thereof, sulfosuccinic acid esters derived from higher fatty acid amides, and salts thereof, represented by the following general formula (2) or (3).

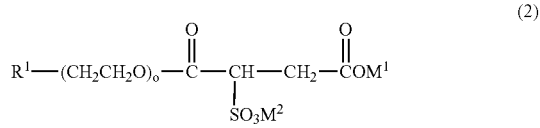

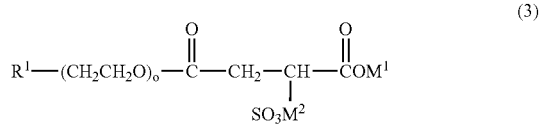

In the formulae, $R^1$ represents $R^2$—O— or $R^3$—CONH—, in which $R^2$ represents a straight-chain or branched-chain alkyl or alkenyl group having 8 to 22 carbon atoms, and $R^3$ represents a straight-chain or branched-chain alkyl or alkenyl group having 7 to 21 carbon atoms; $M^1$ and $M^2$ independently represent a hydrogen atom or a cation selected from alkaline metal ions, alkaline earth metal ions, ammonium ion and organic ammonium ions; and a represents an integer of 0 to 20.

Specific examples thereof include undecylenoylamidoethyl sulfosuccinic acid salts, sulfosuccinic acid polyoxyethylene lauroylethanolamide ester salts, sulfosuccinic acid lauryl salts, polyoxyethylene sulfosuccinic acid lauryl salts, oleic acid amide sulfosuccinic acid salts, etc.

Examples of the above-mentioned monobasic acid type organic sulfonic acid salt-type anionic surfactants include straight-chain or branched-chain alkyl or alkenyl sulfonic acid salt-type having 8 to 22 carbon atoms; alkylbenzene sulfonic acid salts with a straight-chain or branched-chain alkyl group having 10 to 16 carbon atoms; and N- or O-acyl sulfonic acid salts whose acyl group is a residue of a straight-chain or branched-chain, saturated or unsaturated fatty acid having 8 to 22 carbon atoms.

Specific examples thereof include alkane sulfonic acid salts, α-olefin sulfonic acid salts, alkylbenzene sulfonic acid salts, acylmethyltaurine salts, isethionic acid fatty acid ester salts, α-sulfonated fatty acid ester salts and the like.

Examples of sulfuric acid ester salt-type anionic surfactants include alkyl sulfuric acid salt- or ether sulfuric acid salt-type anionic surfactants, and the like.

The above-mentioned alkyl sulfuric acid salt-type anionic surfactant is the salt of a sulfuric acid ester with a straight-chain or branched-chain, saturated or unsaturated higher alcohol having a carbon atom number of 8 to 22, and examples thereof include lauryl sulfuric acid salts, myristyl sulfuric acid salts, oleyl sulfuric acid salt-type, etc.

The above-mentioned ether sulfuric acid salt-type anionic surfactant is an alkylene oxide adduct with the above alkyl sulfuric acid salt, and examples thereof include polyoxyethylene lauryl ether sulfuric acid salts, polyoxyethylene myristyl ether sulfuric acid salts, polyoxyethylene oleyl ether sulfuric acid salts, etc.

Examples of phosphoric acid salt-type anionic surfactants include monoalkyl or monoalkenyl phosphoric acid salts and dialkyl or dialkenyl phosporic acid salts. The alkyl or alkenyl group is an alkyl or alkenyl residue of a saturated or unsaturated fatty acid having 8 to 22 carbon atoms. Examples of such fatty acids include lauric acid, myristic acid, palmitic acid, stearic acid, and oleic acid, with a single composition. Further, the alkyl or alkenyl group may be an alkyl or alkenyl residue of natural mixed fatty acids such as coconut oil fatty acids, tallow fatty acids, hydrogenated tallow fatty acids, castor oil fatty acids, olive oil fatty acids and palm oil fatty acids, or synthetic fatty acids (including branched-chain fatty acids).

Examples of base components of these various anionic surfactants include alkaline metals such as sodium, potassium, and the like; alkaline earth metals such as magnesium, calcium, and the like; organic amines such as monoethanolamine, diethanolamine, triethanolamine, 2-amino-2-methyl-1-propanol, 2-amino-2-methyl-1,3-propanediol, and the like; inorganic amines such as ammonia and the like; basic amino acids such as lysine, ornithine, arginine and the like; and the like. These base components may be used singly or in combination of two or more thereof.

Examples of the Component (B) silicate monomers to be used according to the present invention include alkoxysilanes (silicon alkoxides), water glasses, colloidal silicas, aerosol silicas, precipitated silicas, etc. Preferred among them are alkoxysilanes, water glasses and colloidal silicas, and more preferred are alkoxysilanes.

The alkoxysilanes are represented by the following general formula (4).

$$(R^1O)_m-Si-X_n \quad (4)$$

In the formula, m represents an integer of 2 to 4, n represents an integer of 0 to 2, the sum of m and n is 4, and X represents a hydrogen atom or $R^2$. $R^1$ and $R^2$ each represent a straight-chain or branched-chain alkyl, alkylene, or aralkyl group. For example, alkoxysilanes having, as $R^1$ or $R^2$, a hydrogen atom, a methyl group, an ethyl group, a propyl group, etc. can be used according to the present invention. Among them, preferred are such alkoxysilanes wherein $R^1$ and $R^2$ are the same methyl or ethyl groups, and more preferred is tetraethylorthosilicate (TEOS) wherein $R^1$ and $R^2$ are the same ethyl groups.

Examples of the Component (C) basic silane to be used according to the present invention include, for example, amino group-containing alkoxysilanes. Among them, preferred are trialkoxysilanes with an aminoalkyl terminal group or a quaternary alkylammonium terminal group represented by the following general formula (1), and more preferred are 3-aminopropyltriethoxysilane (APTES), 3-aminopropyltrimethoxysilane (APTMS), and 3-trimethylammonium propyl triethoxysilane (TMAPTES).

$$(R^1O)_3Si-X-NR^2R^3R^4 \quad (1)$$

In the formula, $R^1$, $R^2$, $R^3$ and $R^4$ represent a straight-chain or branched-chain alkyl group or a hydrogen atom, and X represents a straight-chain or branched-chain alkylene group.

The carbon atom number of $R^1$ is preferably 0 to 10 ($R^1$ is H when the carbon atom number is 0) to increase the reactivity and not to inhibit the micelle structure after elimination, though it is not particularly restricted. $R^2$ and $R^3$ have to electrostatically interact with the negative charge of the anionic surfactant, and thereby the carbon atom number thereof may be 0 to 10, preferably 0 to 5 ($R^2$ or $R^3$ is H when the carbon atom number is 0). And, likewise, the carbon atom number of $R^4$ may be 0 to 10, preferably 0 to 5. When $R^4$ has the carbon atom number of 0, the Component (C) basic silane is a primary, secondary or tertiary amine. When $R^4$ has the carbon atom number of 1 to 10, the Component (C) basic silane is a quaternary ammonium, which is generally present as the hydrochloride salt, the bromate salt, the acetate salt, etc. X may have various structures though it is important to select X from the viewpoint of space control. When X is a carbon chain, the carbon atom number of the carbon chain is preferably 1 to 10 from the viewpoints of controlling space between the micelle structure and the silica layer, and fixing the structure, though it is not particularly restricted.

Relationships among a mesoporous silica complex produced from these components, a mesoporous silica outer shell and a mesoporous silica are illustrated in FIG. 1.

The mesoporous silica complex may be produced by a common mixing method wherein Components (A), (B) and (C) are mixed in a solvent. The mesoporous silica complex is generally produced by the steps of dissolving Component (A) in a solvent, mixing Components (B) and (C) therewith, and leaving the resultant mixture at a predetermined temperature for a predetermined period of time.

In general, the solvent to be used for producing the mesoporous silica complex may be water or a solvent containing a mixture of a water-miscible organic solvent and water. From the viewpoint of accelerating the formation of the self-assembly of the Component (A) anionic surfactant, the solvent is preferably water alone or a mixed solvent of water and one or more of various alcohols to increase the solubility of the anionic surfactant, more preferably water alone, or a mixed solvent of water-ethanol or water-methanol.

The mesoporous silica complex is generally produced at a temperature within the range of room temperature to the boiling temperature of the solvent. The temperature is preferably the Krafft temperature of the Component (A) anionic surfactant or more, more preferably 50 to 100° C., from the viewpoints of accelerating the mixing and the reaction.

The period of time for producing the mesoporous silica complex is generally within the range of 1 to 168 hours. The period is preferably 24 to 96 hours, more preferably 48 to 72 hours, from the viewpoints of hydrolyzing and condensation-polymerizing the silicate monomer under the basic conditions.

The pH value upon the production of the mesoporous silica complex is generally 3 or less, or 8 or more. The pH value is preferably 8 or more, more preferably 9 to 10, such that the hydrolysis and condensation polymerization of the silicate monomer are accelerated under the basic conditions, and the amino group of Component (C) is protonated to be capable of interacting with the head moiety of the Component (A) anionic surfactant.

In the production of the mesoporous silica complex of the present invention, one or more types of the Component (A) anionic surfactants may be used. The anionic surfactant may be present in the solution at any concentration as long as it can form the three-dimensional micelle structure. The anionic surfactant concentration of the solution is generally 0.01 to 30 weight %, preferably 0.2 to 10 weight %, more preferably 1.2 to 2.0 weight %.

Further, the ratio of Component (A) to the total of Components (A), (B) and (C) is generally 0.01 to 50 mole %, preferably 0.05 to 20 mole %, more preferably 1 to 10 mole %.

In the production of the mesoporous silica complex of the present invention, the ratio of the Component (B) silicate monomer to the total of Components (A), (B) and (C) is generally 0.1 to 98 mole %, preferably 1 to 95 mole %, more preferably 10 to 90 mole %.

In the production of the mesoporous silica complex of the present invention, the ratio of the Component (C) basic silane to the total of Components (A), (B) and (C) is generally 0.1 to 98 mole %, preferably 1 to 95 mole %, more preferably 10 to 90 mole %.

In the production of the mesoporous silica complex of the present invention, the ratio of Component (C) to the total of Components (B) and (C) is 1 to 90 mole %, preferably 5 to 80 mole %, more preferably 10 to 70 mole %.

Further, in the production of the mesoporous silica complex of the present invention, the mole ratio of Component (C) to Component (A) is 0.5 to 20, preferably 1 to 10.

The generation of the mesoporous silica complex during the production can be confirmed by powder X-ray diffraction. The thus-produced mesoporous silica complex may be washed with an acidic aqueous solution, a water-miscible organic solvent, or an aqueous solution thereof, to obtain the mesoporous silica outer shell of the present invention, and may be calcined to produce the mesoporous silica. In addition, the mesoporous silica complex is expected to be used in cosmetics, paints, building materials, and the other various composite materials as a water- or solvent-retaining material. Further, it is expected that the mesoporous silica complex is used for a film or a thin membrane.

The mesoporous silica outer shell can be produced by washing the mesoporous silica complex with an acidic aqueous solution, a water-miscible organic solvent, or an aqueous solution thereof.

Various solvents may be used for the acid treatment generally. The solvent for the acid treatment is preferably a polar solvent, more preferably water or an alcohol, from the viewpoint of retaining the structure of the mesoporous silica outer shell.

The acid treatment is generally carried out at a temperature within the range of room temperature to the boiling temperature of the solvent. The temperature is preferably room temperature to $100°$ C., more preferably room temperature to $80°$ C., from the viewpoints of retaining the structure of the mesoporous silica outer shell, the yield of the mesoporous silica outer shell, and the boiling point of the solvent for the acid treatment.

The acid treatment is generally carried out for a period of time within the range of 1 to 72 hours. The period is preferably 8 to 48 hours, more preferably 24 to 48 hours, from the viewpoints of retaining the structure of the mesoporous silica outer shell, and the yield of the mesoporous silica outer shell.

The acid treatment pH value is generally within the range of 0 to 4. The pH value is preferably 0 to 2, more preferably 0 to 1, from the viewpoints of retaining the structure of the mesoporous silica outer shell, and the yield of the mesoporous silica outer shell.

Various common acids may be used for the acid treatment. Examples of the acids include hydrochloric acid, acetic acid, nitric acid, sulfuric acid, oxalic acid, and phosphoric acid. The acid for the acid treatment is preferably hydrochloric acid, acetic acid, nitric acid or sulfuric acid, more preferably hydrochloric acid or acetic acid, from the viewpoint of the yield of the mesoporous silica outer shell.

The generation of the mesoporous silica outer shell during the production can be confirmed by powder X-ray diffraction, nitrogen adsorption-desorption measurement, observation with an electron microscope, etc. The thus-produced mesoporous silica outer shell may be converted into the mesoporous silica. In addition, the mesoporous silica outer shell is expected to be used as a material, which adsorb-separates a particular molecule by using the amino group of Component (C) as an adsorption group and by utilizing interaction of the mesoporous space formed by templating the self-organized structure of the anionic surfactant, or as a composite material containing a particular substance adsorbed. Further, it is expected that the mesoporous silica shell is converted into a film or a thin membrane.

The mesoporous silica can be produced by calcining the mesoporous silica outer shell or the mesoporous silica complex.

The calcination temperature is generally within the range of 300 to $900°$ C. The calcination temperature is preferably 400 to $650°$ C., more preferably 500 to $600°$ C., from the viewpoints of retaining the structure of the mesoporous silica and removing the surfactant completely.

The calcination time is generally within the range of 2 to 24 hours. The calcination time is preferably 4 to 12 hours, more preferably 6 to 10 hours, from the viewpoint of removing the surfactant completely.

The thus-produced mesoporous silica can be used as a catalyst, an adsorbent, etc., as ones produced by known conventional methods.

In the case where the mesoporous silica is used as a catalyst, an adsorbent, etc., 2 or 3 of the mesoporous silica complex, the mesoporous silica outer shell, and the mesoporous silica of the present invention may be simultaneously used in combination as long as there are no objections.

EXAMPLE

The present invention will be described in more detail below with reference to Examples without intention of restricting the scope of the invention.

First, the cases wherein sodium dodecyl sulfate (SDS) was used as the surfactant will be described below.

Example 1

Production of Mesoporous Silica Complex 1.447 g of sodium dodecyl sulfate (SDS) surfactant was added to a mixed solvent of ion-exchanged water (162 g) and ethanol (46.1 g), and stirred at $60°$ C. until the mixture became a uniform solution. Then, a mixture of 5.5 g of 3-aminopropyltriethoxysilane (APTES) and 5.2 g of tetraethyl orthosilicate (TEOS) was added to the solution, and further stirred for 1 hour. The aqueous solution was left at $100°$ C. for 2 days after the stirring, whereby white precipitates appeared in the solution. The precipitates were isolated by suction filtration, dried at $100°$ C. overnight, to obtain a mesoporous silica complex.

Figure 2:
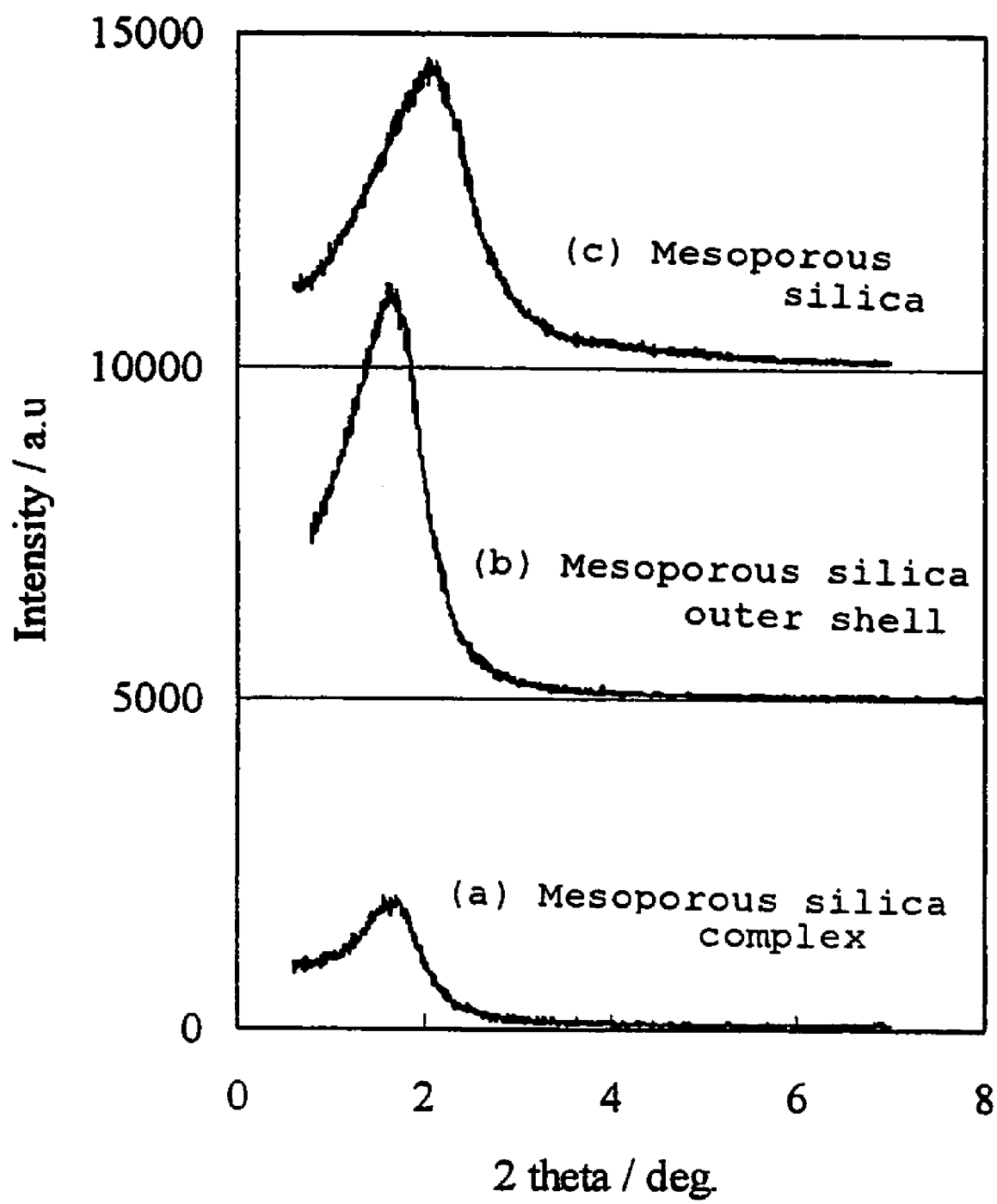
FIG. 2 shows the X-ray diffraction patterns of a mesoporous silica complex, a mesoporous silica outer shell and a mesoporous silica.

As shown in FIG. 2(a), XRD suggested that the mesoporous silica complex was high in periodic structural regularity. However, the high order diffraction line for identifying the mesostructure was unclear, so that the mesoporous silica complex seemed to have such a structure that the channels of the mesopores were disorderly arranged.

Example 2

Production of Mesoporous Silica Outer Shell 5.2 g of 35% concentrated hydrochloric acid was added to a solution of 1 g of the mesoporous silica complex produced in Example 1 in 50 ml of ethanol, stirred at room temperature for 2 hours, and then filtered to collect the resultant powder. These procedures were repeated twice to increase the surfactant extraction ratio. The powder was dried at 100° C. overnight to obtain a mesoporous silica outer shell.

Figure 3:
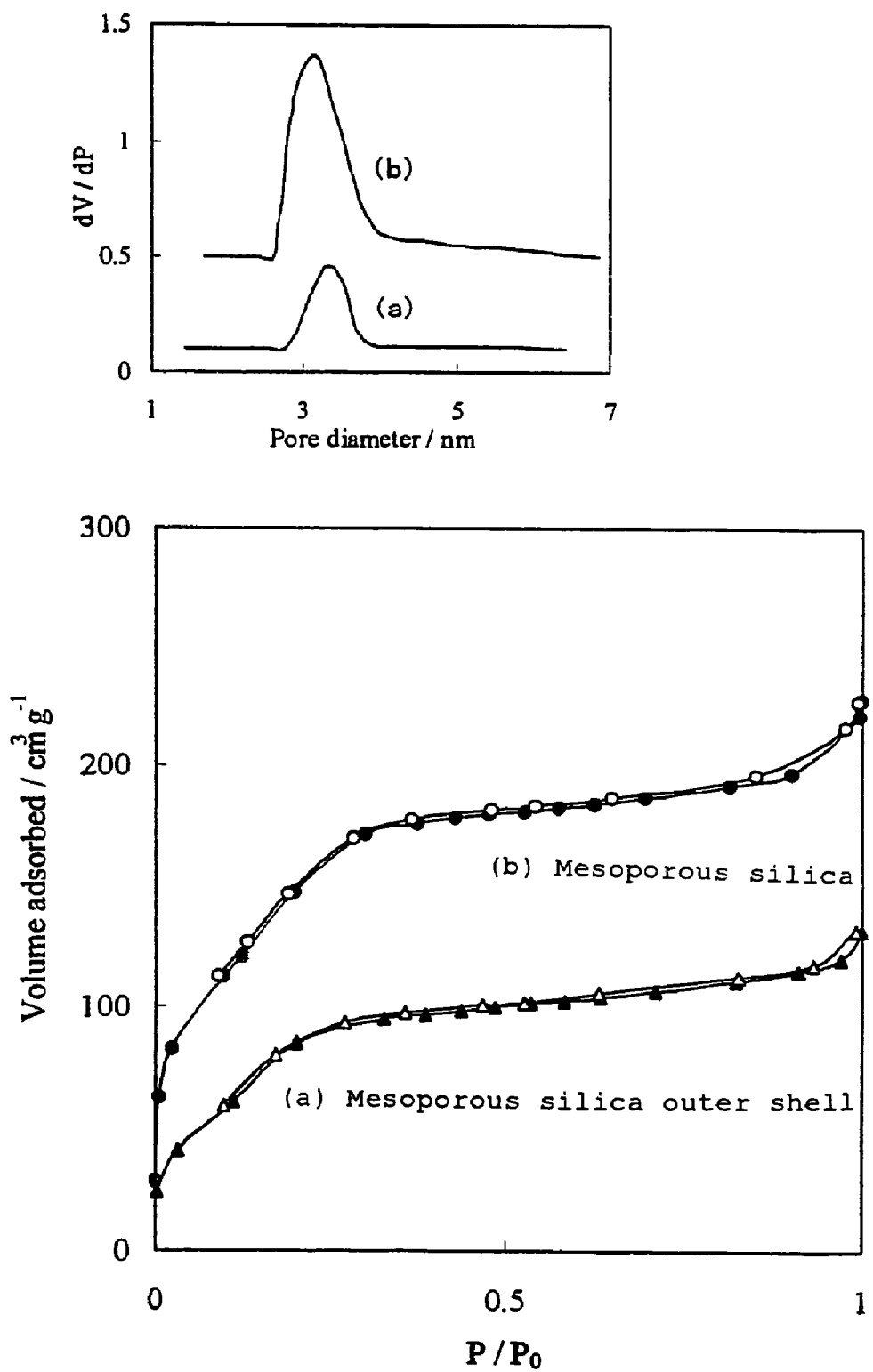
FIG. 3 shows the $N_2$ adsorption-desorption isotherms of a mesoporous silica outer shell and a mesoporous silica. The pore size distributions thereof are also shown therein.

As shown in FIG. 2(b), XRD suggested that the acid-treated sample was high in periodic structural regularity as with the mesoporous silica complex. However, the high order diffraction line for identifying the mesostructure was unclear, so that the mesoporous silica outer shell seemed to have such a structure that the channels of the mesopores were disorderly arranged. As shown in FIG. 3(a), the acid-treated sample showed a IV type $N_2$ adsorption-desorption isotherm and a uniform pore size distribution. The specific surface area (BET method) and the average pore size (D-H method) were 274 $m^2/g$ and 3.2 nm, respectively. Further, as a result of CHNS elemental analysis, 89% of the anionic surfactant, Component (A), was extracted by the acid treatment. As a result of $^{13}C$ CP-MAS NMR analysis, the resonance peaks attributable to the carbon atoms of $\equiv Si-{}^{\alpha}CH_2{}^{\beta}CH_2{}^{\gamma}CH_2NH_3Cl^-$ were observed at $10^{\alpha}$, $21^{\beta}$, and $43^{\gamma}$ ppm, whereby it was confirmed that the aminopropyl group was present in the mesoporous silica outer shell without being decomposed. It was found also in view of the results of the $N_2$ adsorption-desorption measurement that the amount of the aminopropyl group remaining in the sample after the acid treatment was 3.4 mmol/g, and the surface concentration thereof was 7.5 $nm^{-2}$.

It was expected from these results that the obtained mesoporous silica outer shell could be used as a material for adsorbing and isolating a particular molecule by using the amino group of Component (C) as an adsorption group, or as a composite material containing a particular substance adsorbed.

Example 3

Production of Mesoporous Silica

The mesoporous silica complex produced in Example 1 was calcined at 550° C. for 10 hours to obtain a mesoporous silica.

As shown in FIG. 2(c), XRD suggested that the mesoporous silica was high in periodic structural regularity as with the mesoporous silica complex. However, the high order diffraction line for identifying the mesostructure was unclear, so that the mesoporous silica seemed to have such a structure that the channels of the mesopores were disorderly arranged. The TEM image Showed a wormhole (worm-eaten spot) structure of mesochannels with poor regularity, the result corresponding to the result of XRD. As shown in FIG. 3(b), the calcined sample showed a IV type $N_2$ adsorption-desorption isotherm and a uniform pore size distribution. The specific surface area (BET method) and the average pore size (D-H method) were 501 $m^2/g$ and 3.3 nm, respectively.

Then, the cases wherein N-lauroyl-L-glutamic acid was used as the surfactant will be described below.

Example 4

0.7 g of N-lauroyl-L-glutamic acid surfactant was added to 110 g of ion-exchanged water, and stirred at 60° C. until the mixture became a uniform solution. Then, a mixture of 0.9 g of 3-aminopropyltrimethoxysilane (APTMS) and 7.5 g of tetraethyl orthosilicate (TEOS) was added to the solution, and further stirred for 20 minutes.

The aqueous solution was left at 60° C. for 1 day after finishing the stirring, whereby white precipitates appeared therein. The precipitates were isolated by suction filtration, and dried at 100° C. overnight to obtain a mesoporous silica complex. The mesoporous silica complex was calcined at 600° C. for 6 hours to obtain a desired porous mesoporous silica.

Figure 4:
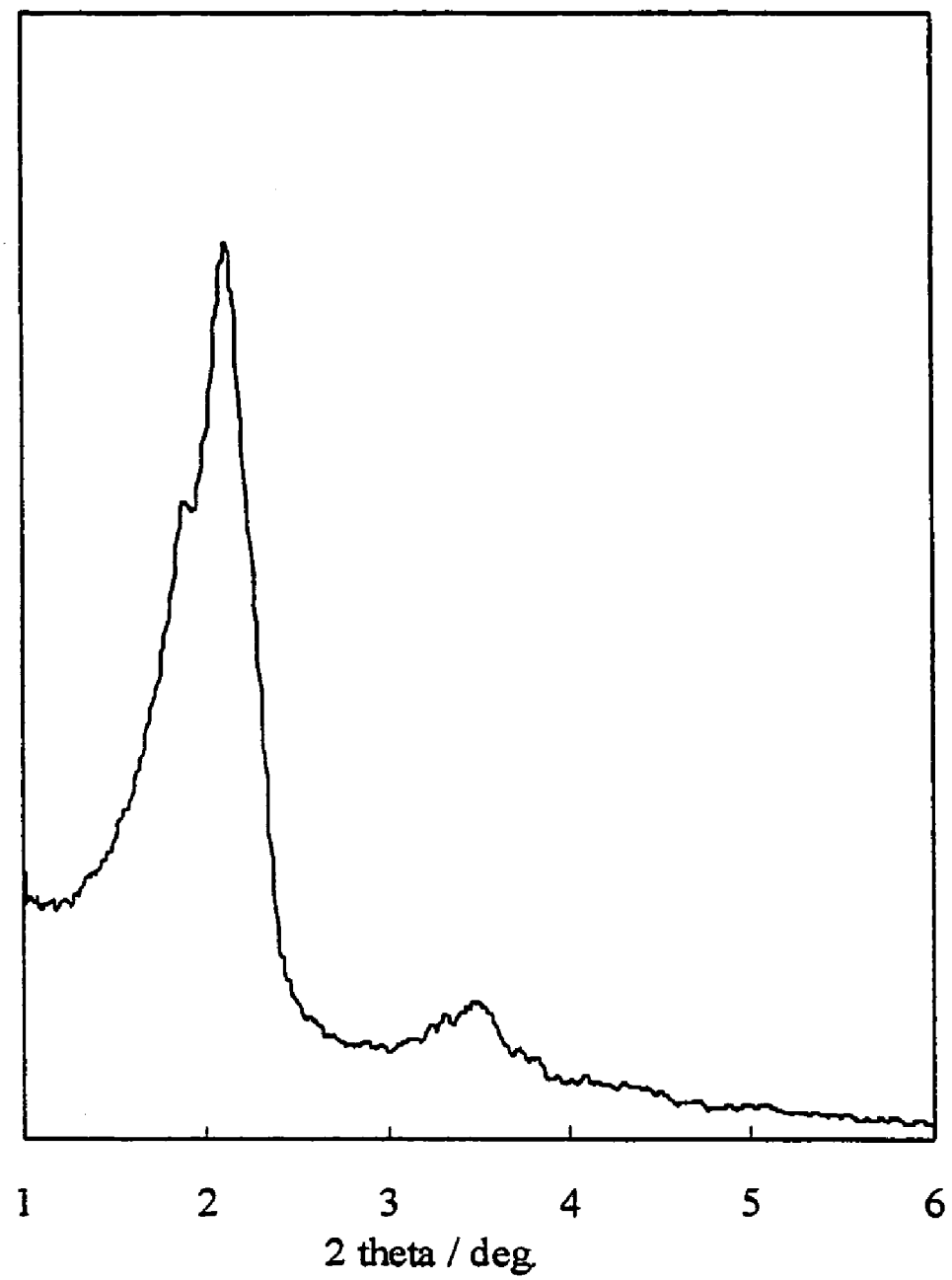
FIG. 4 shows the X-ray diffraction pattern of a mesoporous silica.

In the X-ray diffraction pattern for the mesoporous silica of Example 4 (FIG. 4), two diffraction peaks, which could be indexed as 200 and 210 of 3d-Cubic Pm3n structure, respectively, were observed in a region of $2\theta=1$ to 3. Thus, it was confirmed that three-dimensional channels according to the 3d-Cubic Pm3n structure were formed in the mesoporous silica of Example 4.

Figure 5:
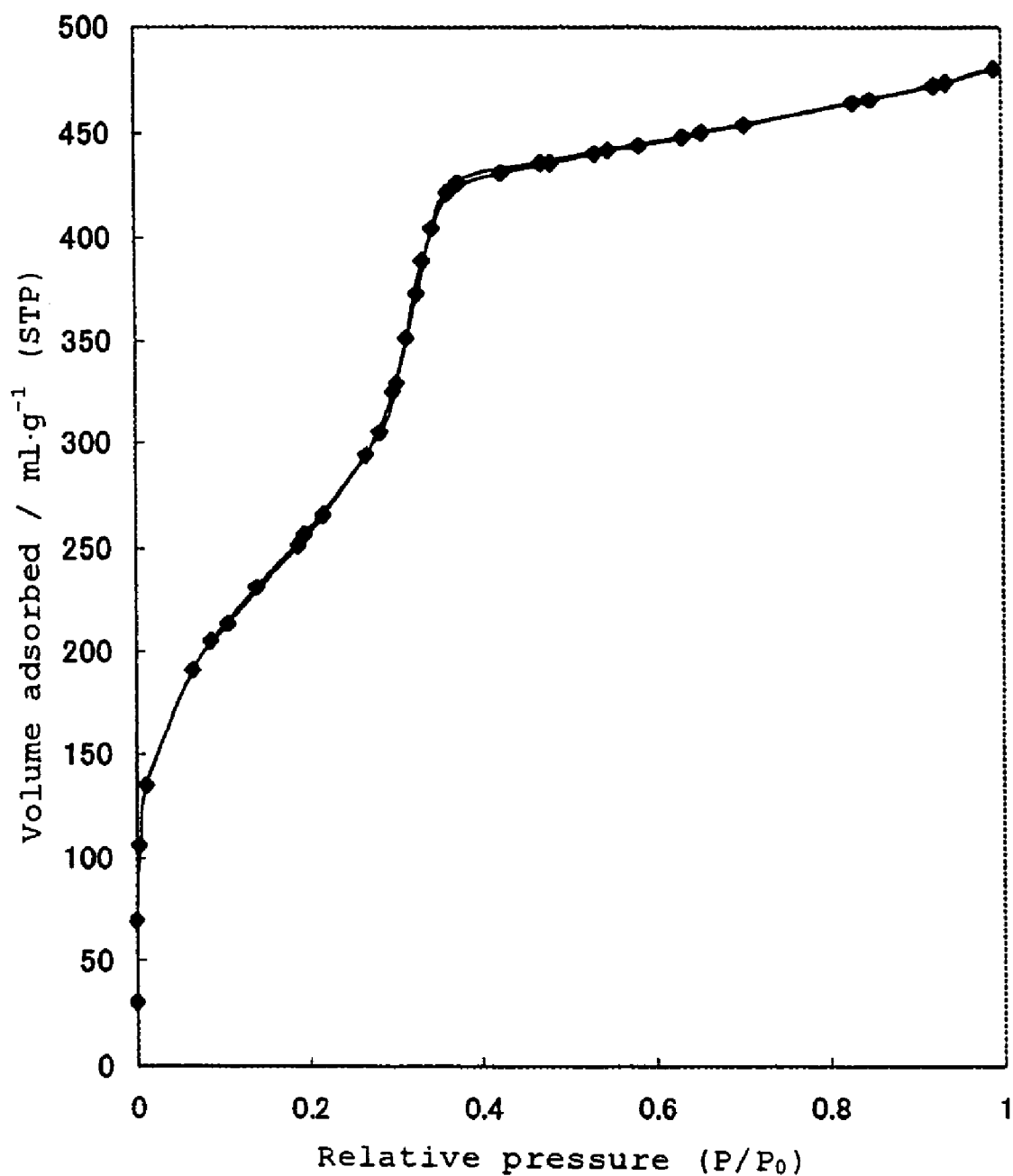
FIG. 5 shows the $N_2$ adsorption isotherm of a mesoporous silica.
Figure 6:
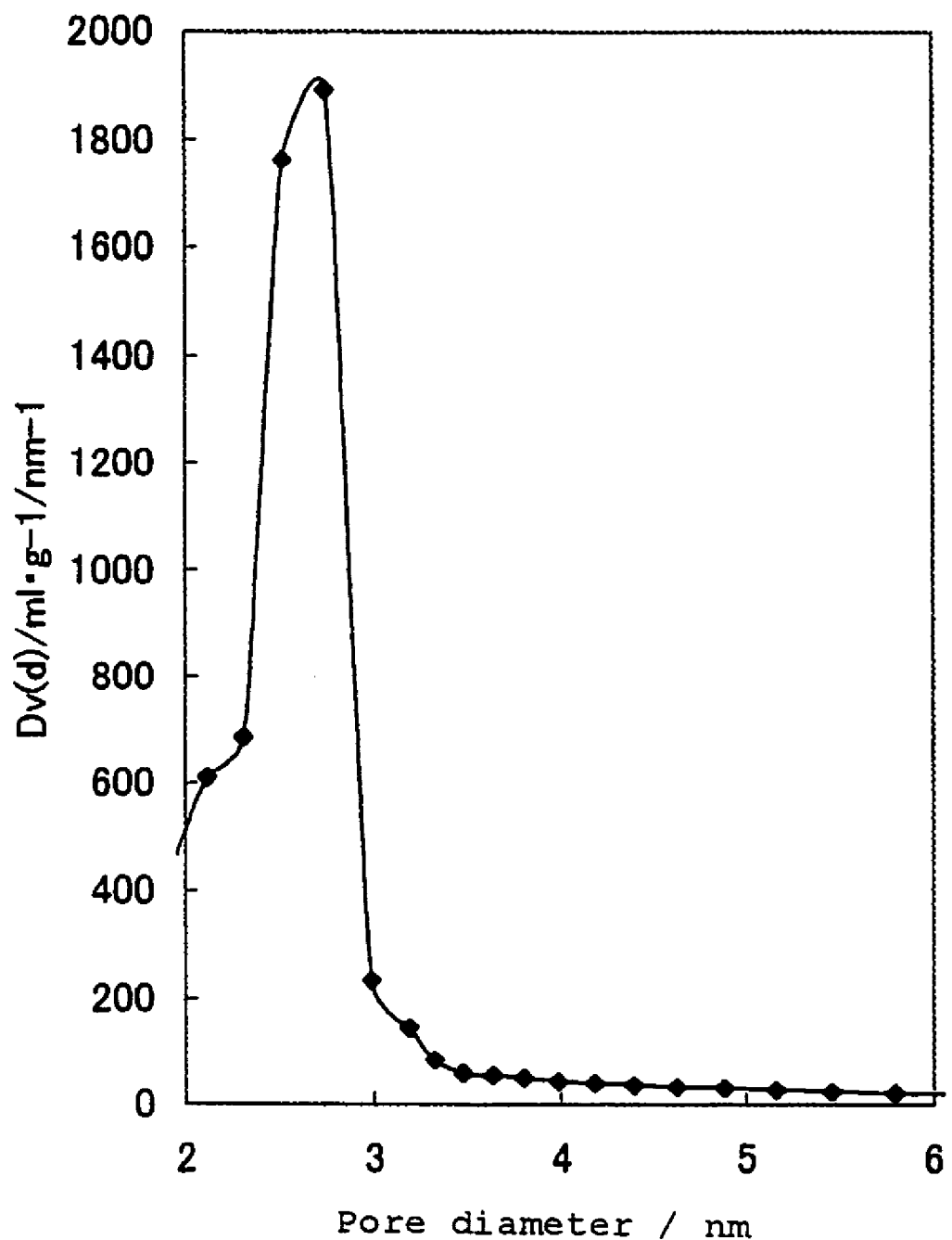
FIG. 6 shows the pore size distribution curve of a mesoporous silica.

The $N_2$ adsorption isotherm of the mesoporous silica of Example 4 was shown in FIG. 5, and the pore size distribution curve thereof obtained by D-H method was shown in FIG. 6. Further, the BET specific surface area, the center pore diameter, and the pore volume obtained based on these measurement results were 963 $m^2/g$, 750 $mm^3/g$ and 2.8 nm, respectively. It was confirmed from these results that the sufficiently uniform porous structure with a large surface area was formed in the mesoporous silica of Example 4.

Example 5

0.7 g of N-lauroyl-L-glutamic acid surfactant was added to 110 g of ion-exchanged water, and stirred at 60° C. until the mixture became a uniform solution. Then, a mixture of 1.4 g of 3-aminopropyltrimethoxysilane (APTMS) and 10.4 g of tetraethyl orthosilicate (TEOS) was added to the solution, and further stirred for 20 minutes.

The aqueous solution was left at 60° C. for 1 day after the stirring, whereby white precipitates appeared therein. The precipitates were isolated by suction filtration, and dried at 100° C. overnight to obtain a mesoporous silica complex. The mesoporous silica complex was calcined at 600° C. for 6 hours to obtain a desired mesoporous silica.

Figure 7:
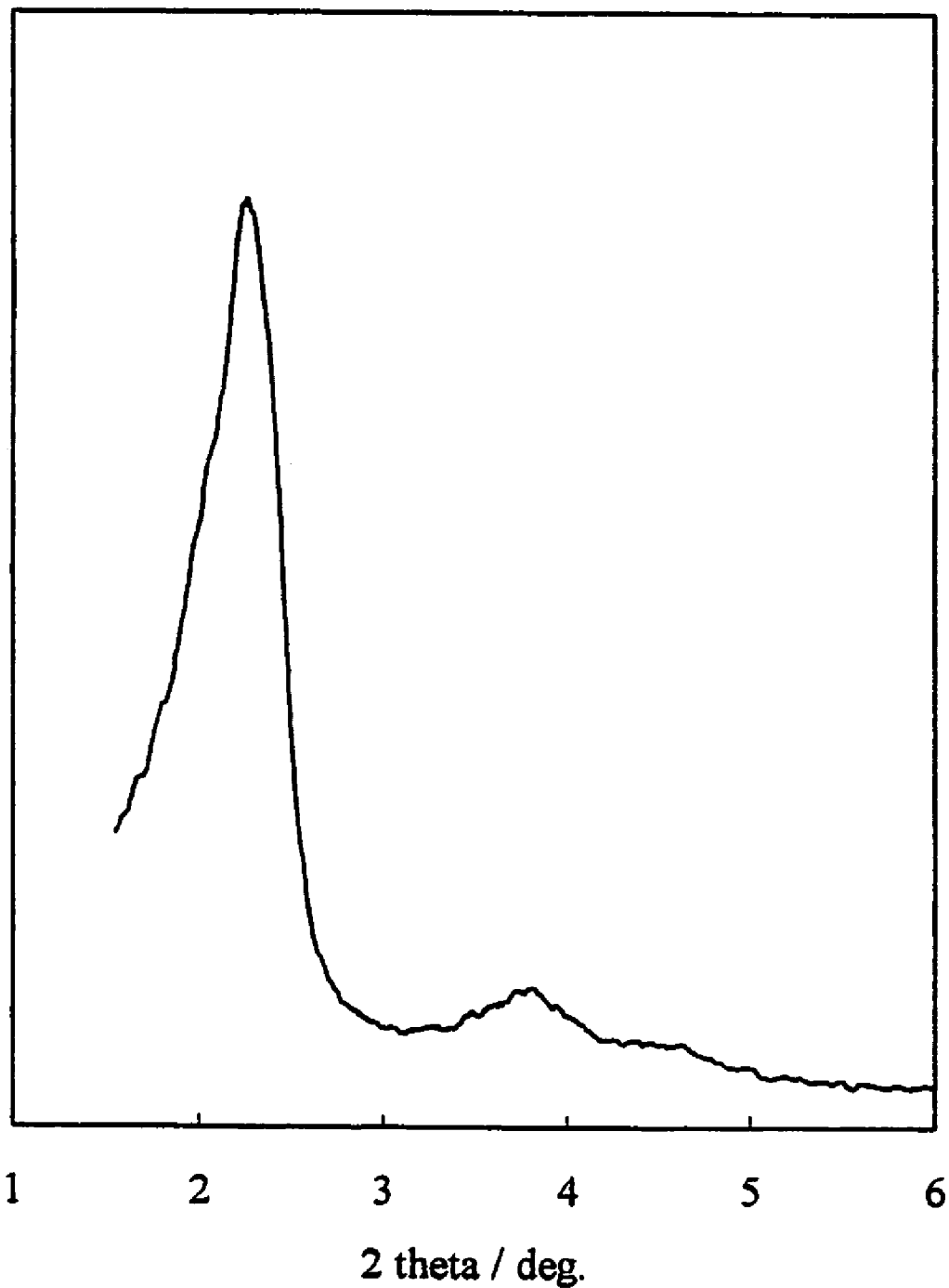
FIG. 7 shows the X-ray diffraction pattern of a mesoporous silica.

The X-ray diffraction pattern for the mesoporous silica of Example 5 was shown in FIG. 7. In FIG. 7, three diffraction peaks observed in the region of 2θ-1 to 5 could be indexed to 10, 11, and 20 of 2d-Hexagonal p6 mm structure, respectively. Thus, it was confirmed that two-dimensional channels according to the 2d-Hexagonal p6 mm structure were formed in the mesoporous silica of Example 5.

Figure 8:
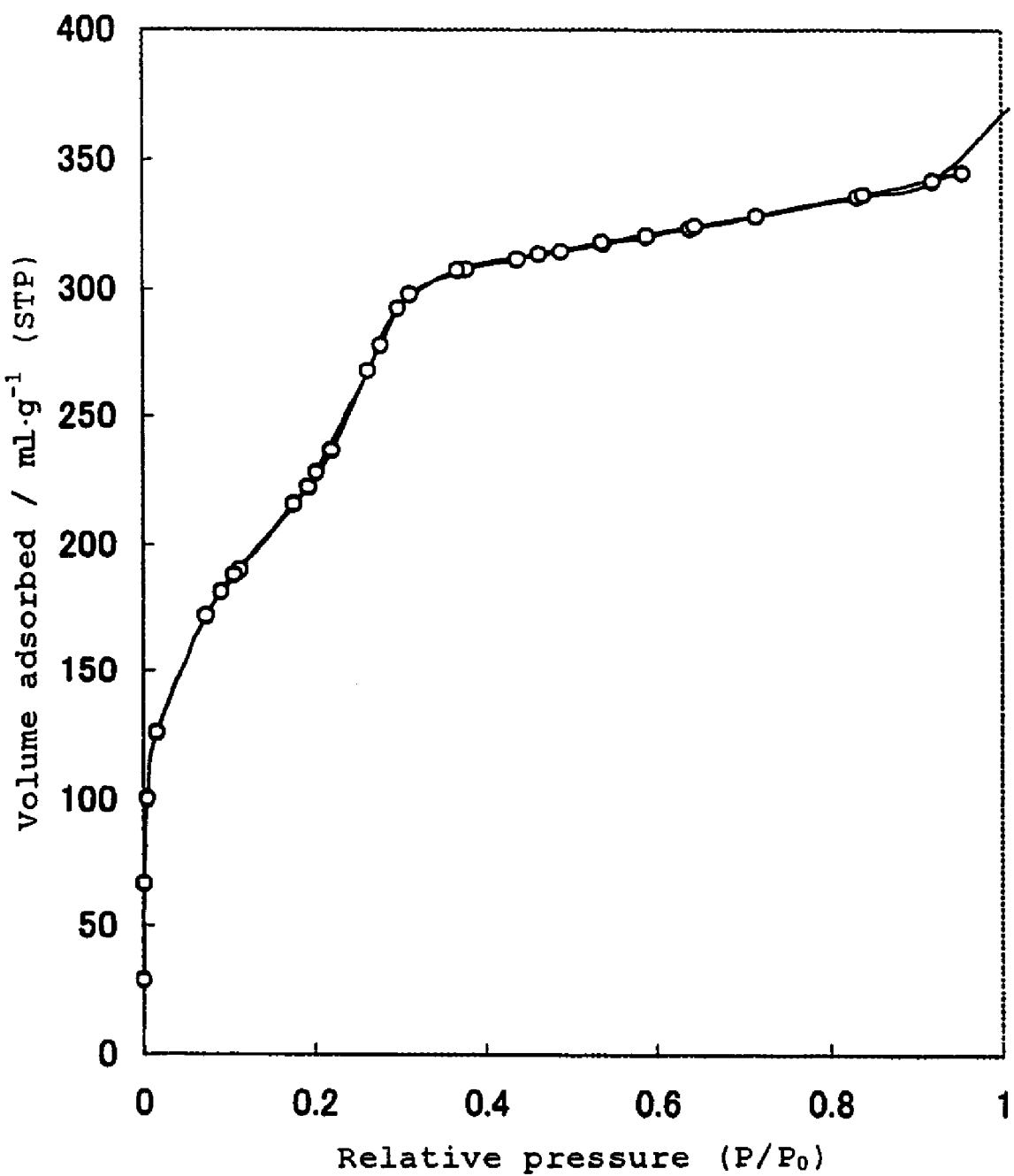
FIG. 8 shows the $N_2$ adsorption isotherm of a mesoporous silica.
Figure 9:
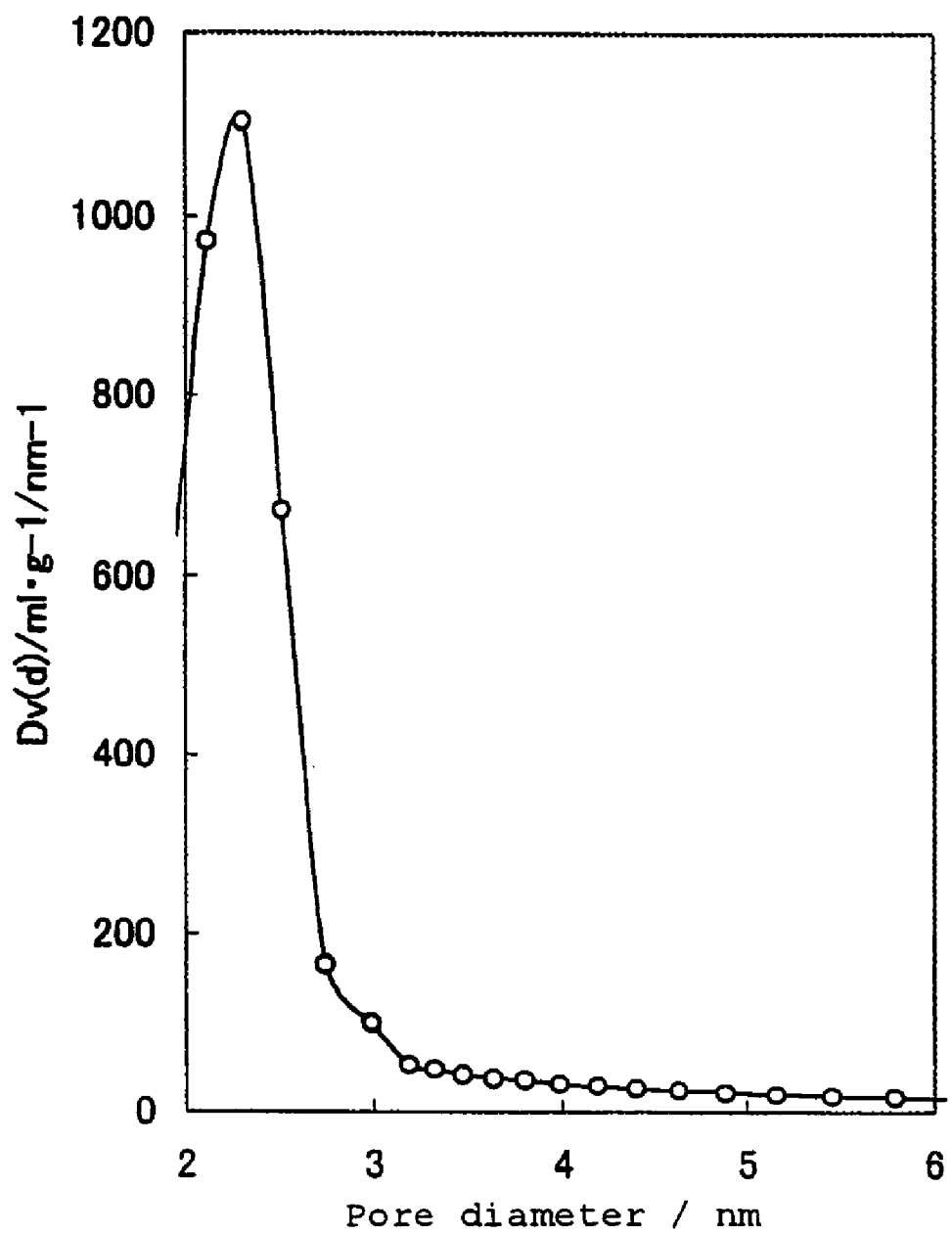
FIG. 9 shows the pore size distribution curve of a mesoporous silica.

The $N_2$ adsorption isotherm for the mesoporous silica of Example 5 was shown in FIG. 8, and the pore size distribution curve thereof obtained by D-H method was shown in FIG. 9. Further, the BET specific surface area, the center pore diameter, and the pore volume were obtained based on these measurement results as 795 $m^2/g$, 498 $mm^3/g$, and 2.3 nm, respectively. It was confirmed from these results that the sufficiently uniform porous structure with a large surface area was formed in the mesoporous silica of Example 5.

Examples 6-12 and Comparative Examples 1-4

Results obtained in the same manner as in Example 1 except for changing the mole ratio of Components (B) and (C) will be shown in the following Table 1. In Table 1, Component (A) was SDS, Component (B) was TEOS, and Component (C) was APTES, as with Example 1.

TABLE 1

| | Mole ratio of Components | | | Comments on regularity of silica structure | | |
|---|---|---|---|---|---|---|
| | (A) | (B) | (C) | Complex | Outer shell | Porous silica |
| Comparative Example 1 | 0.1 | 0.0 | 1.0 | x (No precipitates) | — | — |
| Comparative Example 2 | 0.1 | 0.1 | 0.9 | x (No precipitates) | — | — |
| Comparative Example 3 | 0.1 | 0.2 | 0.8 | Δ (Lamellar) | x (Disintegration) | x (Disintegration) |
| Example 6 | 0.1 | 0.3 | 0.7 | ○ | ○ | ○ |
| Example 7 | 0.1 | 0.4 | 0.6 | ○○ | ○○ | ○○ |
| Example 8 | 0.1 | 0.5 | 0.5 | ○○ | ○○ | ○○ |
| Example 9 | 0.1 | 0.6 | 0.4 | ○○ | ○○ | ○○ |
| Example 10 | 0.1 | 0.7 | 0.3 | ○○ | ○○ | ○○ |
| Example 11 | 0.1 | 0.8 | 0.2 | ○ | ○ | ○ |
| Example 12 | 0.1 | 0.9 | 0.1 | ○ | ○ | ○ |
| Comparative Example 4 | 0.1 | 1.0 | 0.0 | x (No precipitates) | — | — |

○: Powder X-ray peak was observed.
○○: Particularly sharp powder X-ray peak was observed.

As was clear from the results of Comparative Example 4, formation of an ordered silica structure templating the self-assembled SDS structure was not observed in the case of using no Component (C), which is an essential substance according to the present invention. The same results were obtained also in the case of using no Component (C) in Example 4, and thus the basic silane APTES of Component (C) was fundamental to formation of an ordered silica structure.

Further, as was clear from the results of Comparative Examples 1, 2, and 3 shown in the table, formation of ordered silica structure was not observed also in the case where Component (C) is large excess to Component (B).

Example 13

Here we report a novel anionic surfactant templating route to mesoporous silica, which is different from the previous pathways. The organoalkoxysilane with quaternary ammonium organic group (N-trimethoxylsilylpropyl-N,N,N-tributylammounium) has been used as the structure directing agent of zeolites ZSM-5 and ZSM-11 (H. X. Li, M. A. Camblor, M. E. Davis, *Maicroporous Mater*. 3, 117 (1994)). Our approach is based on the co-structure-directing effect imparted with aminosilane or quaternized aminosilane. We prove this effect by using 3-aminopropyltrimethoxysilane (APS) or N-trimethoxysilylpropyl-N,N,N-trimethylamonium chloride (cation denoted here as TMAPS) (FIG. 10). The negatively charged head group of the anionic surfactants interacts with the positively charged ammonium site of APS and TMAPS electrostatically, through the neutralization of the various acids (pKa=2-6) and APS (pKb≈3.4), and double decomposition of anionic surfactant salt and TMAPS quaternary ammonium salt, respectively (FIG. 10). The alkoxysilane sites of APS and TMAPS are co-condensed with tetraalkoxysilane, e.g., tetraethoxylsilane (TEOS), to be assembled subsequently to form the silica framework. The trimethylene groups of the APS and TMAPS covalently tether the silicon atoms incorporated into the framework to the cationic ammonium groups. It can be considered that proper CSDA(co-structure-directing agent)/anionic surfactant molar ratio could result in the pH of the system favorable for the condensation of alkoxysilane. Either secondary or tertiary aminosiliane (pKb≈3.2-4.2) can be substituted for APS.

This novel templating route produced well ordered novel structures, which have never been reported. The mesostructures possessed uniform pore diameters ranging from 2.0 to 6.2 nm. Typical anionic surfactant in the form of carboxylic acid and their salts, corresponding CSDA, synthesis conditions and obtained mesophases are listed in Table 2. Well-ordered AMS-n silicas have been synthesized in the pH range of 8.5-10.2 resulting from the proper CDSA/anionic surfactant molar ratio. Obviously, the effective head-group area of anionic surfactant is decreased in the following order: N-acyl-glutanate>N-acyl-alanate>N-acyl-glycinate≈carboxylate.

The overall topology of mesostructure is determined by the geometry of the surfactant including chain length and head-group area. TMAPS with a large head-group has been found to be effective in forming the higher curvature mesophases. Sulfuric and phosphoric acid and their salt anionic surfactants have also led to ordered mesostructures in combination with either APS or TMAPS. The combination of sodium salts of anionic surfactants and APS (T. Yokoi, H. Yoshitake, T. Tatsumi, *Chem. Mater.* Submitted) or that of amino acids and TMAPS resulted in disordered mesoporous silicas.

In a typical synthesis, a mixture of 4.16 g TEOS and 1.03 g TMAPS (50% in methanol) was added to a mixture of 0.56 g of $C_{16}AS$ (for the surfactants abbreviation, see Table 2) and 56 g of deionized water with stirring at 60° C. After the mixture was stirred for 24 h, the mesostructured product formed was cured at 100° C. for 1-3 days. The products were filtered and dried at 333 K. The anionic surfactants were removed by exhaustive solid-liquid extraction using 15 vol. % $H_2O$/ethanol solutions at boiling temperature overnight to give the mesoporous materials with pendant amino or ammonium groups. Both of the anionic surfactants and the organics of the CSDA used were removed by calcination at 650° C. for 6 h.

TABLE 2

Synthesis conditions and obtained mesophases.

| Surfactant | Gel composition* | | | |
|---|---|---|---|---|
| Acid | APS/Sur | Si/Sur | pH value | Mesophase |
| $C_{12}$GluA, $C_{14}$GluA, | 2-8 | 15-20 | 8.9-9.5 | AMS-2 |
| $C_{18}$GluA, $C_{12}$AlaA, $C_{14}$Ala, $C_{12}$GlyA, $C_{14}$GlyA, $C_{16}$GlyA, $C_{12}$AA, $C_{14}$AA | 1-8 | 7.5-12 | 8.8-10.2 | AMS-3 |
| $C_{12}$AlaA | 0.75-1 | 6-7.5 | 9.2-9.4 | AMS-4 |
| $C_{12}$-$C_{14}$AlaA, $C_{12}$-$C_{16}$GlyA, $C_{12}$-$C_{16}$AA | 1 | 3-5 | ~9.4 | AMS-5 |

| Sodium salt | TMAPS/Sur | Si/Sur | | |
|---|---|---|---|---|
| $C_{12}$GluS, $C_{14}$GluS, | 2 | 15 | 8.9-9.5 | AMS-1 |
| $C_{12}$AlaS, $C_{12}$GlyS, $C_{12}$AS | 1 | 7.5 | 8.9-9.5 | AMS-2 |
| $C_{16}$GluS, $C_{18}$GluS, $C_{14}$GlyS, $C_{16}$GlyS, $C_{12}$AlaS, $C_{14}$AlaS, $C_{14}$AS, $C_{16}$AS, | 1 | 7.5 | 8.5-9.5 | AMS-3 |

*The well-ordered AMS-n silicas have been synthesized with 1.0 weight % surfactants at 60° C. for 1 day.

$C_n$XY
- A: Free acid, S: Sodium Salt
- Glu: L-Glutamic acid, Gly: Glycine, Ala: L-Alanine
- $C_nH_{2n-1}O$ ($C_{12}H_{23}O$: N-Lauroyl, $C_{14}H_{27}O$: N-Myristoyl, $C_{16}H_{31}O$: N-Palmitoryl, $C_{18}H_{35}O$: N-Stearoyl)

Figure 11:
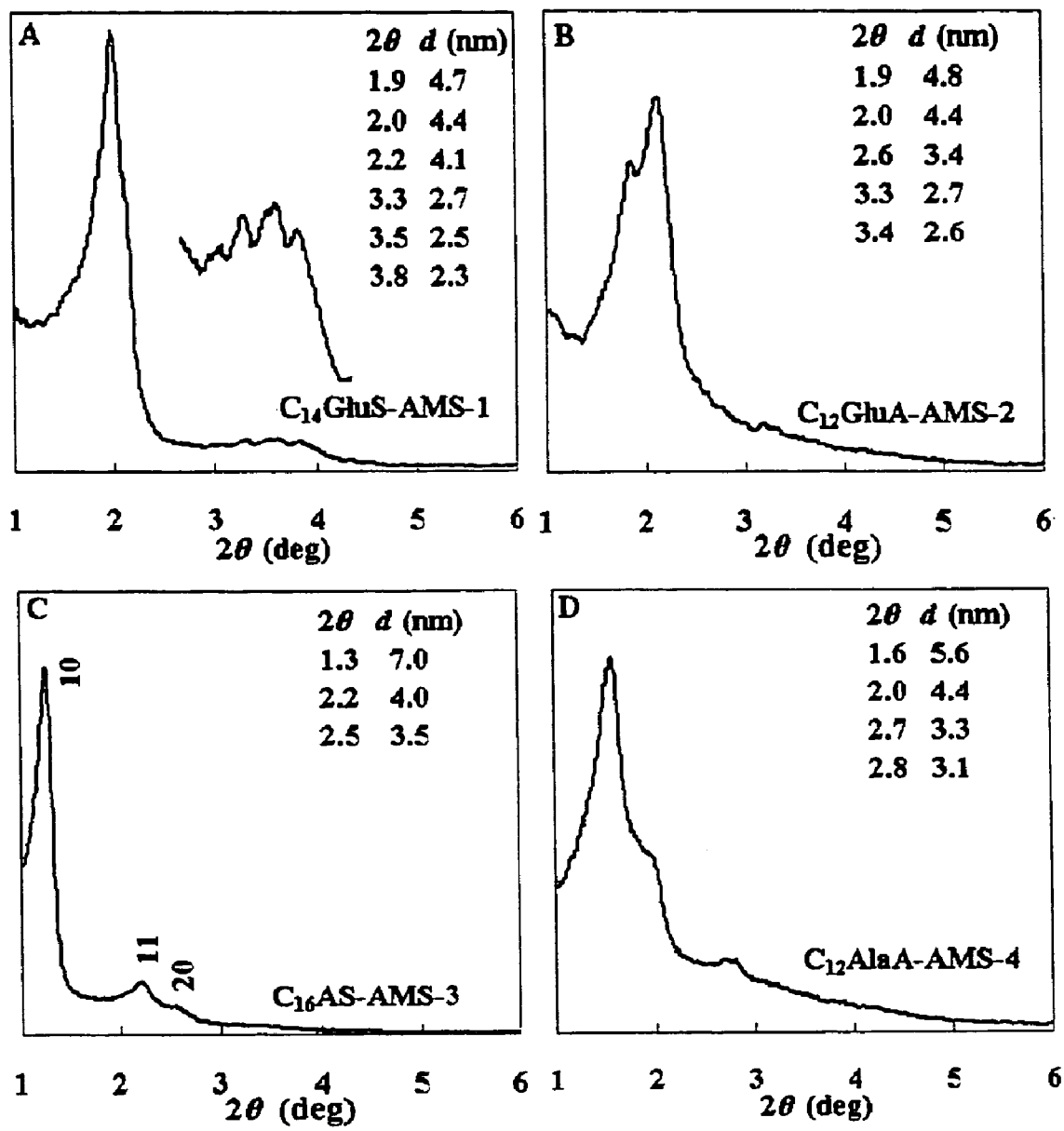
FIG. 11 shows the XRD patterns of calcined mesoporous silicas. The chemical mol composition of the reaction mixture was (A) $C_{14}GluS$-AMS-1$C_{14}GluS$:TMAPS:TEOS:$H_2O$ 1:2: 10:2405 (at 100° C. for 3 d); (B) $C_{12}GluA$-AMS-2: $C_{12}GluA$: APS:TEOS:$H_2O$ 1:2.5:18.5:1905 (at 100° C. for 2 d); (C) $C_{16}AS$-AMS-3: $C_{16}AS$:TMAPS:TEOS:$H_2O$ 1:1:9:1544 (at 60° C. for 1 d); (D) $C_{12}AlaA$-AMS-4, $C_{12}AlaA$:APS:TEOS: $H_2O$ 1:0.75:7.5:1505 (at 60° C. for 1 d). XRD patterns were recorded on an MX Labo powder diffractometer equipped with Cu Kα radiation (40 kV, 20 mA) at the rate of 1.0 deg/min over the range of 1.5-10.0°(2θ).

$C_n$AX
- A: Free acid, AS: Sodium Salt
- $C_nH_{2n-1}O$ ($C_{12}H_{25}$: N-Lauric, $C_{14}H_{29}$: Myristic, $C_{16}H_{33}$: Palmitic, FIG. 11A shows the X-ray diffraction (XRD) pattern of calcined AMS-1 mesoporous silica (denoted as $C_{14}$GluS-AMS-1) synthesized with $C_{14}$GluS surfactant and TMAPS. Three peaks in the range of $2\theta=1.5-3°$ and additional three weak peaks in the range of 3.5° to 6° were observed. These peaks can be indexed either by the cubic phase with unit cell parameter a=7.6+0.4 nm or by the 3d-hexagonal phase with the unit cell parameters, a=5.4±0.4 nm, and c=8.8±0.4 nm. In the latter case, the c/a ratio is 1.65, which is close to the ideal c/a ratio of 1.633 for the hexagonal close-packed (hcp) structure of hard spheres. This material shows a uni-axial cylindrical disc (though some edges can be observed). Therefore, it is reasonable to assume that AMS-1 is 3d-hexagonal. Channels both perpendicular and parallel to the particle surface can be observed and the Fourier diffractograms (FD) suggests the presence of large ordered regions. The corresponding electron diffractogram (inset) is commensurate with 3d-hexagonal symmetry. It is interesting that the particle was surrounded by a layer of different orientation from the inner one, which may block the inner pore system and lead to a decrease in the surface area and pore volume (Table 3).

TABLE 3

Properties of AMS mesoporous silicas synthesized by anionic surfactants templating route.

| Structure | Surfactant, CSDA | Unit cell* (nm) | Surface area $(m^2g^{-1})$† | Pore diameter‡ (nm) | Wall thickness (nm) |
|---|---|---|---|---|---|
| AMS-1 (3d-hexagonal) | $C_{14}$GluS, TMAPS | a = 5.4, c = 8.8 | 501 | 2.3 | |
| AMS-2 (3d-cubic) | $C_{12}$GluA, APS | 9.6 | 963 | 2.8 | |
| AMS-3 (2d-hexagonal) | $C_{16}$AS, TMAPS(EX)§ | 8.1 (9.2) | 387 (311) | 5.2 (6.2) | 2.9 (3.0) |
| AMS-4 (Bicontinuous 3d-cubic) | $C_{12}$AlaA, APS | 13.1 | 760 | 4.0 | |

*Calculated from the XRD patterns.
†Calculated by the BET method.
‡Calculated from the adsorption branch of the $N_2$ isotherm by using the BJH method.
§Extracted sample.

The XRD pattern of calcined AMS-2 mesoporous silicas (denoted as $C_{12}$GluA-AMS-2) synthesized by using $C_{12}$GluA and APS is shown in FIG. 11B. This sample shows two well-resolved sharp XRD diffraction peaks in the region of $2\theta=1.5°-3.0°$; since the ratio of d-spacings of the two peaks is close to 2/√5, these might be indexed to the 200 and 210 reflections (a=9.6±0.4 nm), based on the cubic system.

When the longer-chain surfactants were used for the synthesis, 2d-hexagonal p6 mm mesostructure (AMS-3) with a lower curvature, analogous to MCM-41, were obtained. The typical XRD pattern of the sample (denoted as $C_{16}$AS-AMS-3) synthesized by using $C_{16}$AS with TMAPS are shown in FIG. 11C. It has been confirmed by EM observations that this sample is two-dimensional (not shown).

The monovalent acylaminoacid $C_{12}$AlaA resulted in the bicontinuous 3d-cubic phase ($C_{12}$AlaA-AMS-4) with APS/$C_{12}$AlaA molar ratio of 1.0 (FIG. 11D). Interestingly, bicontinuous 3d-cubic Ia3d phase analogous to MCM-48 was obtained with a low APS/$C_{12}$AlaA molar ratio of 0.75.

A lamellar mesophase (AMS-5) was obtained from the $C_{12}$-$C_{14}$ALaA, $C_{12}$-$C_{16}$GlyA and $C_{12}$-$C_{16}$AA surfactant synthesis systems at high surfactant concentrations and low Si/surfactant molar ratios.

AMS silicas show unique structures with periodic modulations or unusual long-range periodicity, We consider that these modulations may be caused by the coexistence of micelles different in size and curvature possibility including local chirality, suggesting that more than one competing stabilization mechanisms are operative, and that more than one synthetic/mechanistic parameters are involved. The formation of local chiral structure seems to be the most possible reason for their structural modulations, since the novel structures of ASM-1, 2 and 4 were synthesized with the chiral organic surfactants. The formation of different micelle size and curvature can be explained in terms of the interaction of the surfactant molecule tails with APS, considering that ASM-2 and ASM-4 with periodic modulation have been synthesized with APS. The synthesis mechanism is currently being studied by combining with HRTEM image contrast patterns.

Figure 12:
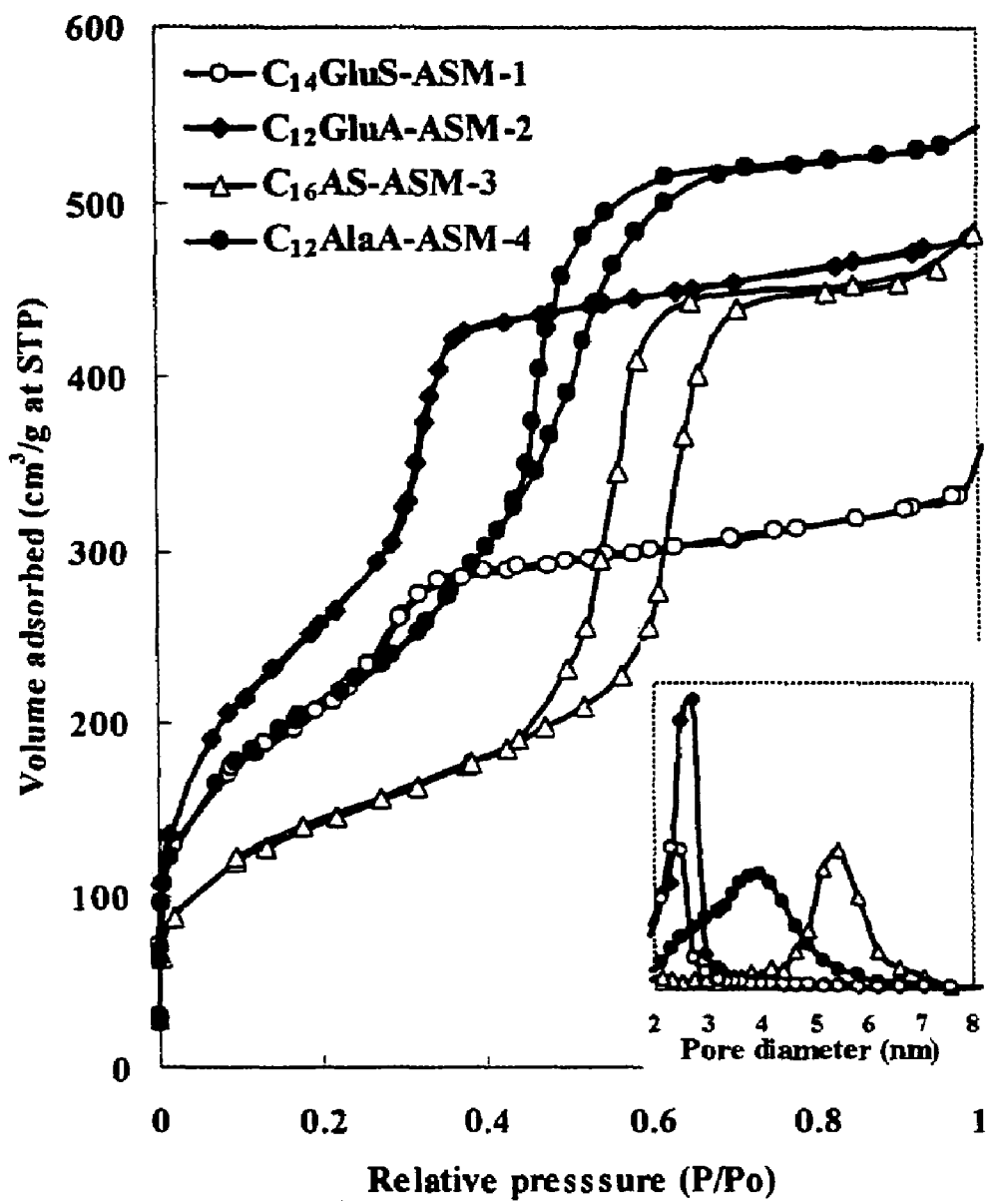
FIG. 12 shows the $N_2$ adsorption-desorption isotherms and BJH pore size distribution distributions of AMS-n mesoporus silica shown in FIG. 11. The isotherms were measured at –196° C. on a Belsorp 28SA sorotionmeter.

All samples with a high periodicity mesostructure as suggested from XRD patterns show type IV isotherm. As shown in FIG. 12, the samples synthesized with different surfactants exhibit sharp capillary condensation steps nitrogen adsorption isotherm, and consequently, narrow mesopore size distributions. The structural properties of the mesoporous silicas are listed in Table 3. The pore diameter and wall thickness is in the range of 2.0 to 6.2 nm and 2.4-3.1 nm (not all shown), respectively.

Figure 13:
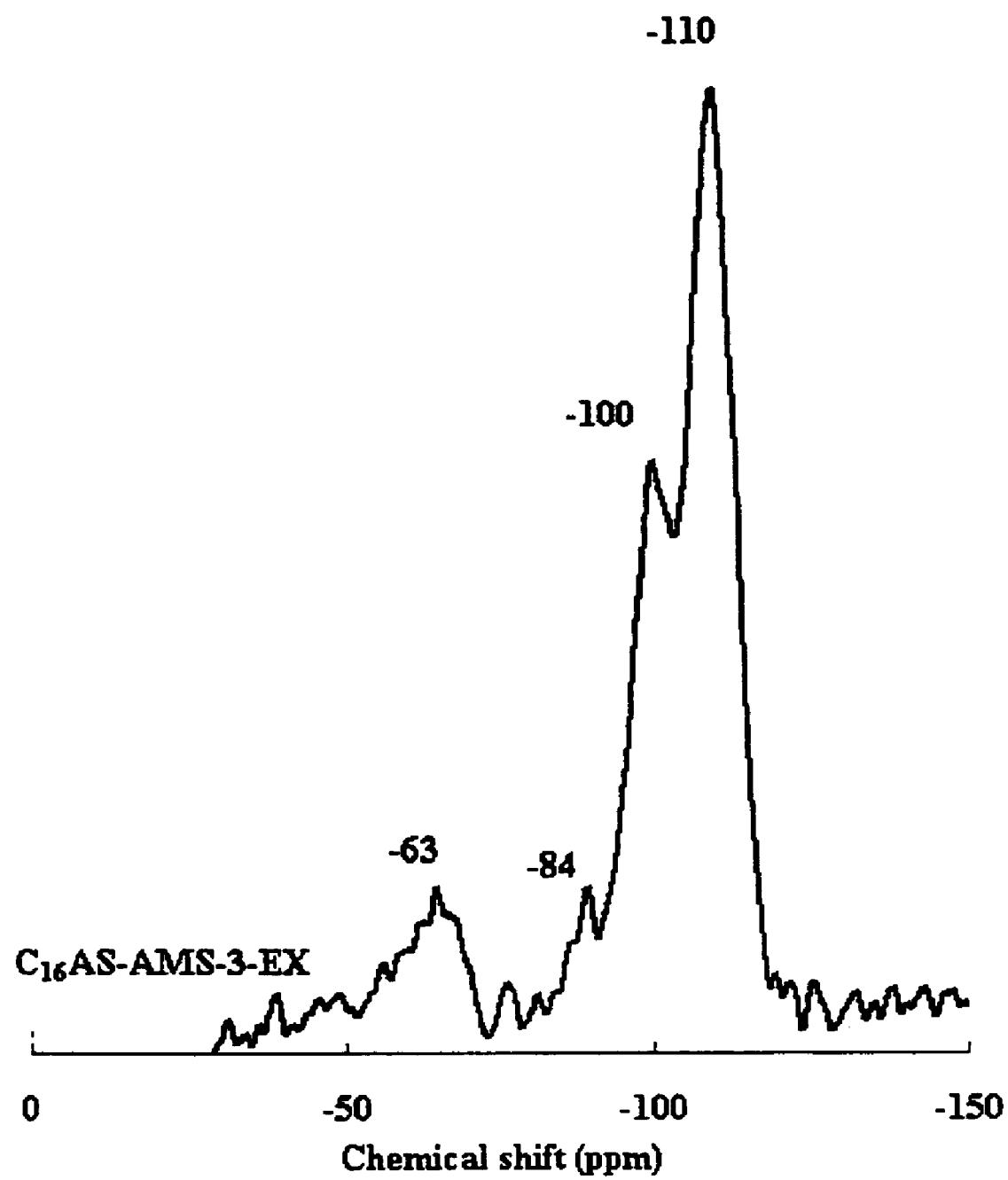
FIG. 13 shows the CP $^{29}Si$ NMR spectra of an extracted AMS-3 silica $C_{16}AS$-AMS-3-Ex. The spectra were collected at a JEOL-LA400WB 400 MHz spectrometer at 79.4 MHz and a sample spinning frequency of 5 kHz, respectively.

The $^{29}$Si NMR spectrums of extracted $C_{16}$AS-AMS-3 silica have been measured (FIG. 13). The peaks at -63 ppm attributed to silicon atom that is bonded to carbon (T″≡Si—C≡) (K. Yamamoto, Y. Sakata, Y. Nohara, Y. Takahashi, T. Tatsumi, Science, 300, 470 (2003)), and the peaks at -84, -100 and -110 ppm attributed to $Q^2$, $Q^3$ and $Q^4$ silicons ($Q^n$=Si(OSi)$_n$(OH)$_{4-n}$), respectively, are observed. Thus, we conclude that the silicon atom in the aminosilane is located within the framework via co-condensation with TEOS. After calcinations of AMS-3 silica in air at 650° C., the $^{29}$Si NMR spectrum shows no resonance of T″ and the $Q^3/Q^4$ ratio decreased.

Attempts to prepare mesoporous silica either by using the simple primary, secondary or tertiary alkylamines in place of APS, or by using simple quaternary ammonium salts in place of TMAPS, in combination with TEOS, were not successful. These results demonstrate the effectiveness of the strategy using silanes with amino or quaternized amino pendant as CSDA to initiate silica condensation at the surface of self-organised anionic surfactants.

Effects of the Invention

The syntheses of the mesoporous silicas with high structural regularity utilizing the anionic surfactant micelle, which had never been reported previously, were achieved for the first time by using the basic silane. The novel route for synthesizing mesoporous silicas of various metal oxides using surfactant micelles was thus established, and thus drastic advancements in the syntheses of mesoporous silicas are expected.

The invention claimed is:

1. A method for producing a mesoporous silica complex having mesopores uniform in size, comprising
    mixing said Components (A), (B) and (C)), wherein
    (A) An anionic surfactant
    (B) A silicate monomer
    (C) A basic silane;
in water or a mixed solvent of a water-miscible organic solvent and water, and wherein
    the ratio of Component (A) to the total of Components (A), (B) and (C) ranges from 0.05 to 20 mole %,
    Component (B):Components (C)=0.3 to 0.9:0.7 to 0.1.

2. A method for producing a mesoporous silica outer shell, comprising
    forming said mesoporous silica outer shell based on the structure of the mesoporous silica complex obtained by the method according to claim 1 as a template, wherein the mesoporous silica complex is washed with an acidic aqueous solution, a water-miscible organic solvent, or an aqueous solution thereof, to remove Component (A).

3. A method for producing a mesoporous silica, comprising the method according to claim 1, further comprising calcining said mesoporous silica complex.

4. A method for producing a mesoporous silica, comprising the method according to claim 2, further comprising calcining said mesoporous silica outer shell.

5. A method for producing a mesoporous silica complex having mesopores uniform in size, comprising
    mixing said Components (A), (B) and (C) according to claim 1, wherein said Component (C) is a basic silane represented by formula (1)

$$(R^1O)_3Si—X—NR^2R^3R^4 \quad (1)$$

wherein $R^1$, $R^2$, $R^3$ and $R^4$ represent a normal or branched alkyl group or a hydrogen atom, and X represents a normal or branched alkylene wherein when $R^4$ has a carbon number of 0, the basic silane corresponds to a primary, secondary or tertiary amine;
in water or a mixed solvent of a water-miscible organic solvent and water.

6. A method for producing a mesoporous silica outer shell, comprising
    forming said mesoporous silica outer shell based on the structure of the mesoporous silica complex obtained by the method according to claim 5 as a template, wherein the mesoporous silica complex is washed with an acidic aqueous solution, a water-miscible organic solvent, or an aqueous solution thereof, to remove Component (A).

7. A method for producing a mesoporous silica, comprising the method according to claim 6, further comprising calcining said mesoporous silica complex.

8. A method for producing a mesoporous silica, comprising the method according to claim 6, further comprising calcining said mesoporous silica outer shell.

9. The method of claim 1, wherein the ratio of Component (A) to the total of Components (A), (B) and (C) ranges from 0.1 to 10 mole %.

* * * * *